United States Patent [19]
Hanulik

[11] 4,405,430
[45] Sep. 20, 1983

[54] REMOTELY OPERABLE SAMPLE-TAKING APPLIANCE, ESPECIALLY FOR ASCERTAINING RADIO ACTIVITY PROFILES IN CONTAMINATED MATERIAL SURFACES

[75] Inventor: Jozef Hanulik, Zurich, Switzerland

[73] Assignee: Gesellschaft zur Forderung der Forschung an der Eidgenossischen Technischen Hochschule, Zurich, Switzerland

[21] Appl. No.: 243,557

[22] Filed: Mar. 13, 1981

[30] Foreign Application Priority Data

Mar. 20, 1980 [CH] Switzerland ............ 2184/80

[51] Int. Cl.³ .................... G01N 27/46
[52] U.S. Cl. .................... 204/400; 204/1 T; 73/864; 73/864.31
[58] Field of Search ........... 204/1 T, 195 R; 73/864, 73/864.31

[56] References Cited

U.S. PATENT DOCUMENTS

| 3,091,967 | 6/1963 | Hurdlow | 73/425 |
| 3,469,639 | 9/1969 | Charlade | 175/78 |
| 3,498,904 | 3/1970 | Williams | 204/284 |
| 3,554,891 | 1/1971 | Duffy et al. | 204/195 R |
| 3,627,664 | 12/1971 | Grimaldi | 204/195 R |
| 3,824,016 | 7/1974 | Woodriff et al. | 356/85 |
| 4,006,063 | 2/1977 | Ensanian | 204/195 R |
| 4,125,440 | 11/1978 | Markovits | 204/195 R |
| 4,190,513 | 2/1980 | Jumer | 204/224 R |

FOREIGN PATENT DOCUMENTS 1192522 5/1965 Fed. Rep. of Germany.
1284524 12/1968 Fed. Rep. of Germany.
2903246 7/1980 Fed. Rep. of Germany.

OTHER PUBLICATIONS

Neeb, "Inverse Polargraphic und Voltammetrie", 1969, pp. 26-29.

Primary Examiner—T. Tung
Attorney, Agent, or Firm—Watson, Cole, Grindle & Watson

[57] ABSTRACT

A sample-taking appliance comprises several sensors (61, 62, 63, 64) arranged on a turntable like sensor carrier (50) in such a manner that the application areas (68) of the small sensor sponges (67) decrease stepwise from the first to the last sensor. By simple rotation of the turntable the sensors (61, 62, 63, 64) can be brought successively into a working position. The sensor carrier (50) is preferably accommodated in a housing (25) which is open at the bottom and which is raisable and lowerable in the frame (5) of the appliance by, for example, a threaded spindle (41, 42). The threaded spindle (41) is driven by an electric motor (44). For each sampling the sensor carrier (50) is lowered until the cell voltage corresponds to a predetermined desired value. This produces sufficiently precise and reproductible measured values of the electrolytic current for ascertaining the removed layer thickness. The appliance makes it possible to take material samples even from locations of high radiation loading. The material layers removed as samples lie concentrically above each other so that the graduation of the application areas (68) comes into full effect and the material samples taken by the small sponges and the radioactivity contained therein are not falsified.

10 Claims, 6 Drawing Figures

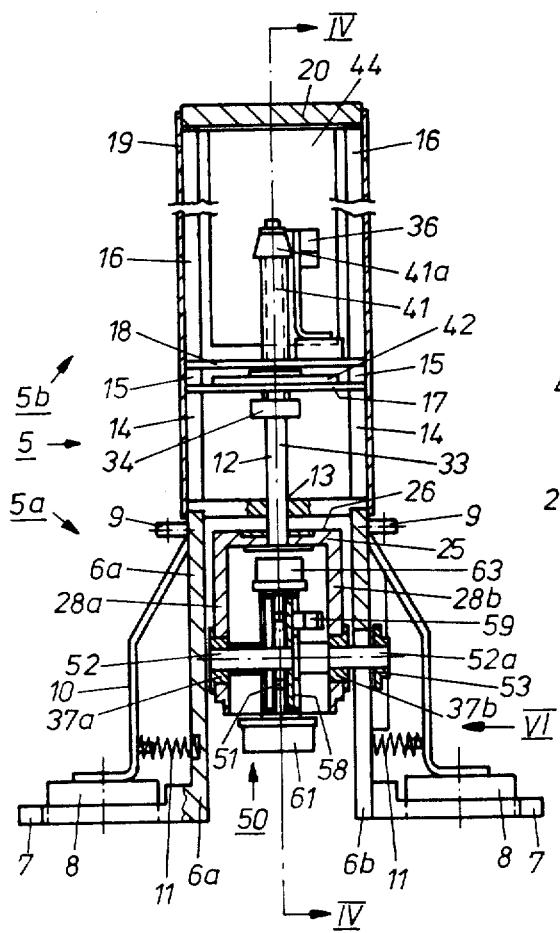
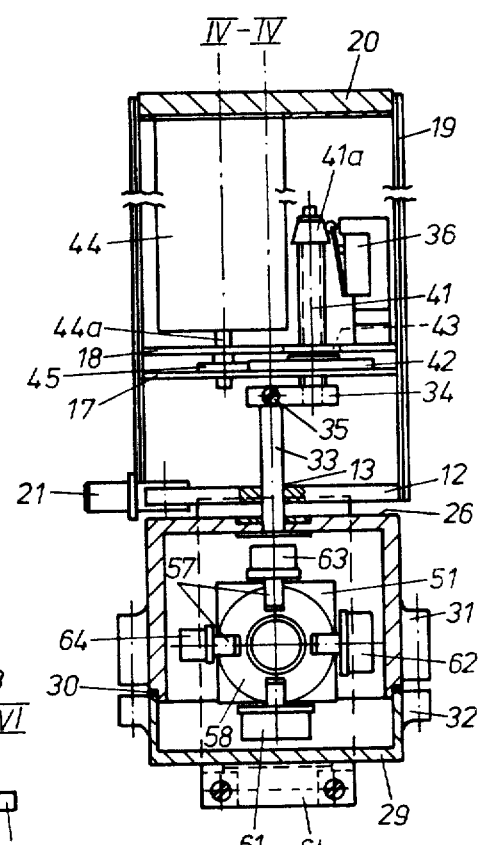
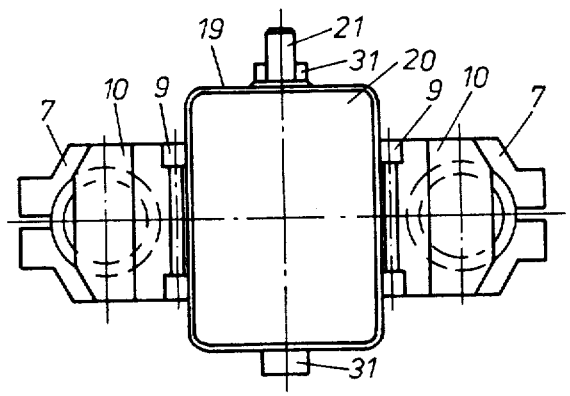
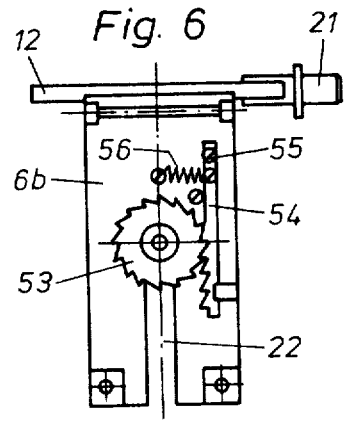

REMOTELY OPERABLE SAMPLE-TAKING APPLIANCE, ESPECIALLY FOR ASCERTAINING RADIO ACTIVITY PROFILES IN CONTAMINATED MATERIAL SURFACES

BACKGROUND OF THE INVENTION

1. Field of the Invention

The invention concerns a remotely operable sample-taking appliance, especially for ascertaining radio activity profiles (characteristics) in contaminated material surfaces and the chemical composition of strata close to the surface, wherein for each sample a layer of material is removed electrolytically from the surface region under investigation by means of a sensor containing an electrolyte-impregnated small sponge, and the removed material is absorbed in the sensor for a subsequent chemical analysis and/or of its radio-activity, in order to produce a radio-activity profile of the surface region from a plurality of successive samples; as well as a method of operating the sample-taking appliance.

2. Prior Art

For example, in nuclear reactor installations as the duration of operation continues component surfaces are increasingly contaminated by fission and activation products carried along by the cooling agent, and as a result of this contamination the servicing of the installation becomes ever more difficult as time goes on, until finally there is a danger of an unacceptably high radiation dosage being received in servicing, and in order to avoid this the installation must be decontaminated. On account of the magnitude of the surface to be decontaminated the decontamination of a reactor circuit system, for example, is an expensive project requiring detailed preparation so that the decontamination can be carried out in the minimum time with minimum possible radioactive fall-out and with an adequate certainty that the residual activity does not at any location exceed the permitted value after decontamination. For such a preparation adequate knowledge of the nature of the surface layer to be decontaminated is necessary and in particular essentially as regards the distribution of the contamination both over the surface and in the depth of the surface layer as well as the chemical composition of the surface layer. In general, the contamination is present either in a loose layer resting on the surface of the component which may easily be removed, for example, by rinsing or is chemically bonded in the material and/or diffused into the material at that region of the component which is close to the surface. In order to obtain the distribution in depth of the contamination the contaminated material can be removed layer-by-layer in a given surface region and the activity for the material of each removed layer can be determined. The activity plotted on a diagram against the layer depth results in an "active profile" of the examined surface region, from which the depth of the layer to be decontaminated can also be extrapolated to obtain the residual activity for the component. Various per se known methods may be used for the removal of the layers, but since the material to be removed may be relatively highly radioactive and the layers to be removed may be very thin, for example up to only a few $\mu$m thick, a chemical, especially electrolytic, method of removal of material is preferable to mechanical removal of material, such as grinding, sandblasting etc. For the electrolytic removal of radioactive material an electrode block lined with a small synthetic plastics sponge impregnated with electrolyte will advantageously be used, which forms an electrolytic cell with the material layer to be removed acting as a counter-electrode, the electrolysis being carried out in such a way that all material is contained in the sponge and can be analysed both chemically and as regards its activity. No particular difficulties arise here for the electrolysis itself, that is, in the selection of the actual electrolyte, for choice of the electrolytic current intensity, the magnitude and polarity of the cell voltage, etc., since comprehensive special literature is available.

An activity profile may of course be only evaluated usefully if it is taken from suitably satisfactory samples on the basis of sufficiently precise measured values, and in the sample-taking there is the additional difficulty that the material is radioactive and under some circumstances even relatively highly active, and thus remote operation must be provided for the sample-taking as well.

SUMMARY OF THE INVENTION

Accordingly, the task for the invention was to produce a remotely operable sample-taking appliance of the above-described kind with which in a selected surface region several material layers may be removed in succession so accurately that separate, unfalsified material samples are obtained; which appliance in the case of appropriate operation also delivers sufficiently precise and reproducible measured values, especially for the electrolytic current, whereby to permit in each case a sufficiently precise determination of the thickness of the electrolytically removed layer.

In accordance with the invention, the above features and advantages are obtained by using at least three sensors; a common current connector connected to the sensors; sponges of graduated sizes of application areas associated respectively with the sensors; a sensor carrier carrying the sensors; an appliance framework in which the carrier is arranged for upward and downward movement, and remotely operable setting devices and lifting devices arranged on the framework and effective to bring the individual sensors successively and sequentially in the order of a decreasing sponge application area into a working position and therefore to lower the sensor in said working position with the sensor carrier to an operative position with defined application pressure of the respective sponge on the surface region to be examined.

A housing may accommodate the sensor carrier and is movable upwardly and downwardly in the framework, with the housing having an underside open but closable by a cover to form a closed transport unit for the sensors. The housing is liquid-tight when closed by the cover and is filled with electrolyte for the impregnation of the sensor sponges before the sample taking operation. The sensor carrier is a turntable rotatable in the housing about an axis of rotation. A rotary plate is secured to the turntable and carries the sensors in an equally spaced arrangement at its circumference. The setting device for the setting of the sensors into the working position is arranged for the rotation of the turntable about the axis of rotation. The turntable is rotatable in the housing about an axis which is perpendicular to the direction of travel of the housing in the framework, with each sensor being located in its working position when in the course of its rotation the turntable has arrived at the lower point of culmination of the latter.

Moreover, the turntable includes a shaft rotatably mounted in the housing with one end of the shaft protruding from the housing. A shift rod is pivotably arranged on the framework, and a stepping wheel cooperating with the stepping wheel rotates the turntable further by one sensor position during the upward stroke of the housing.

The framework may include a threaded spindle connectable to be driven by an electric motor for the upward and downward movement of the sensor carrier. A limit switch is associated in the uppermost position with the threaded spindle by the actuation of which switch the drive motor is switched off or reversed in the direction of rotation thereof. Furthermore, the framework may include feet in the form of either vacuum suction cups or holding magnets for rigidly holding the framework on a base.

In a further modification, there are four sensors which are exchangeably mounted on the sensor carrier.

Advantageous embodiments of the invention are indicated in the subordinate Claims 2-10 and 12, 13.

BRIEF DESCRIPTION OF THE DRAWINGS

The invention will be explained in greater detail below by means of exemplary embodiments with reference to the accompanying drawings, wherein:

FIGS. 3, 4 and 5 respectively show a side elevation, front elevation and plan view of a preferred embodiment of a sample-taking appliance according to the invention, and FIG. 6 shows an elevating device used in this appliance.

DETAILED DESCRIPTION

Figure 1:
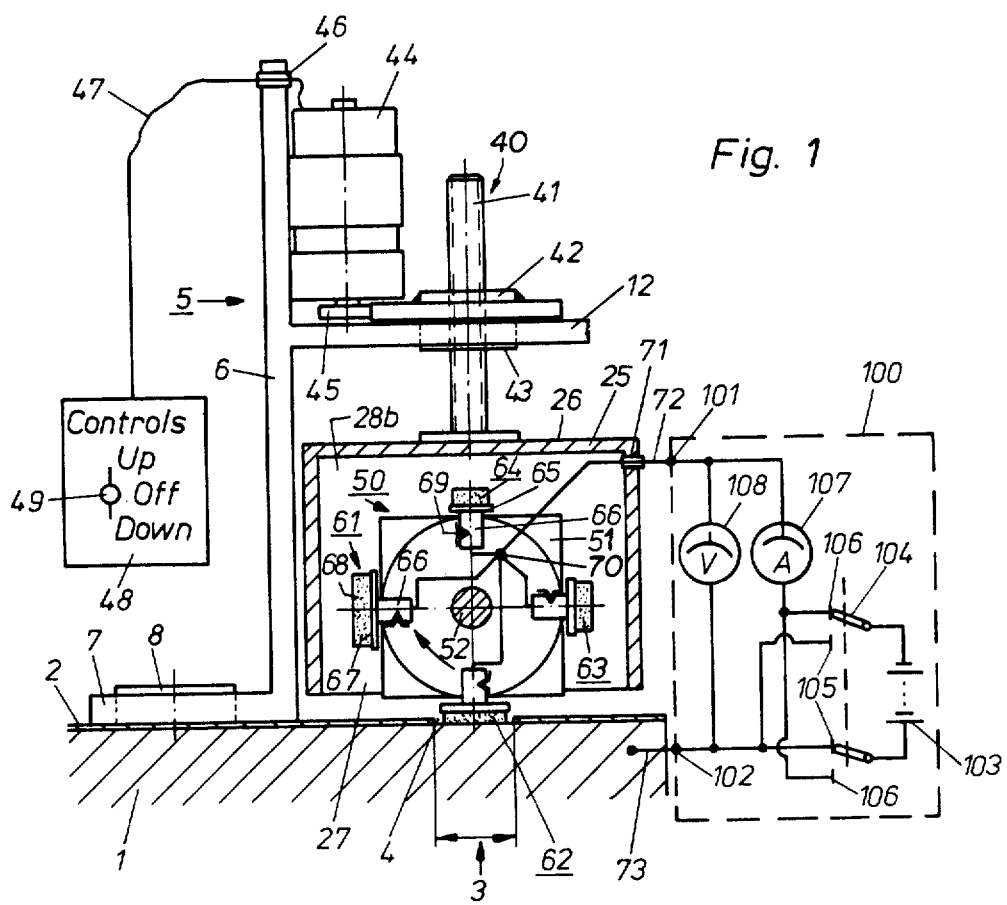
FIG. 1 is a diagrammatic view of a sample-taking appliance according to the invention, with external circuitry connected thereto.

FIG. 1 is a diagrammatic view of a sample-taking appliance according to the invention which is set up, for example, over a contaminated component 1, covered with an oxide layer 2, of a reactor cooling circuit, in order to take material samples by layers from the surface region 3, to establish an activity profile.

The sample-taking appliance an illustrated has an appliance frame especially designated by 5, of which only one-half is shown in FIG. 1 for the sake of greater clarity. The appliance frame 5 comprises essentially two vertical support walls 6 which are inter-connected with one another in their upper region by transverse members, such as for example a carrier plate 12, and at their lower ends carry laterally protruding appliance feet 7 fitted with conventional adhesion devices 8, such as vacuum suction cups or holding magnets, in order to provide firm position to the appliance on the base.

The appliance frame 5 accommodates a parallelepipedic housing 25 of metal or synthetic plastics material which is open at its underside and is upwardly and downwardly moveable by means of an elevating device 40. Any known controllable elevating device arranged for remote operation can be used for the raising and lowering of the housing 25, but for preference a screw spindle or jack 41 is provided which is secured, for example, to the upper side 26 of the housing 25, and the housing 25 can be guided in lateral guides, which are not illustrated in FIG. 1, in order to prevent rotation about the spindle axis. A driving toothed wheel 42 containing the screw nut for the screw jack 41 is rotatably mounted in a bearing plate 43 arranged in the carrier plate 12 and is driven through a toothed wheel gearing 45 by an electric motor 44 with reversible direction of rotation. A connector device 46 secured to the frame 5 of the appliance connects the electric motor 44 to a conductor cable 47 leading to a remotely situated control device 48 which, in the simplest case for manual operation, may comprise a three-position switch 49 for "up", "down" and "off".

The housing 25 comprises a displaceable sensor carrier 50 equipped with at least three sensors, in the illustrated embodiment with four sensors 61, 62, 63, 64. Each sensor 61, 62, 63, 64 consists of an electrode block 65 of cylindrical shape carrying at its rear a shank 66 for the insertion of the sensor into the sensor carrier 50 and at its front a preferably cylindrical small sponge 67, for example of polyethylene foam material. The small sponges 67 of the individual sensors 61, 62, 63, 64 have different diameters, so that their front faces of the small sponges 67 serving as application areas 68 decrease in area from sensor to sensor, the magnitudes of the application areas as provided being about 4 $cm^2$ for the first sensor 61, 3 $cm^2$ for the second sensor 62, 2 $cm^2$ for the third sensor 63 and 1 $cm^2$ for the fourth sensor 64, but of course other size values may also be selected.

The sensor carrier 50 serves to bring the individual sensors 61, 62, 63, 64 successively into a working position in which, when the housing 25 is raised, the application surface 68 of the small sponge 67 lies opposite to the surface region 3 of the contaminated component 1 to be examined and can be applied to the surface region by lowering the housing 25. Any construction suitable for such adjustment of the sensors may be selected for the sensor carrier 50. The sensor carrier 50 as illustrated is made in the form of a turntable having a square rotary plate 51 in the four sides of which the four sensors 61, 62, 63, 64 are inserted with their shanks 66, the sensors 61, 62, 63, 64 being held fast in the rotary plate 51 by retaining springs 69 cooperating with the shanks 66. The rotary plate 51 of the turntable is secured on a shaft 52 which is rotatably mounted in the housing walls 28a, 28b perpendicularly to the direction of raising of the housing 25, that is to say perpendicularly to the axis of the screw jack 41. A remotely operable or automatically acting drive device is provided to rotate the turntable and is arranged so that, starting from a basic position in which the sensor 61 with the largest application area 68 is disposed in the working position, the further sensors are brought by rotation, preferably in one direction, in succession with application surfaces decreasing in size into the working position, but which drive device can be of any desired kind. Thus, for example, an electric motor can be provided externally on the housing 25 and may be controlled, for example, so that it can be switched on only when the housing is raised and at every switching-on it rotates the turntable shaft 51 through a specific angle, through 90° in the illustrated embodiment with four sensors, which can be achieved without difficulty by the provision of limit switches and of arresting-locking devices which precisely determine the end positions of the turntable.

The sensors 61, 62, 63, 64 are connected by one pole through a conductor connection 70 to a connector 71 leading through the housing 25, which connector is connected by an electric lead 72 with an external circuit arrangement 100 arranged remotely. To explain the manner of operation of this sample-taking appliance, let it be assumed that the external circuit arrangement 100 is present only, so to speak, in primitive or basic equipment and comprises a direct-current source 103 for a working voltage of about 12 V, a pole-changer switch 104 connected to the poles of the direct-current source 103 with two fixed contact pairs 105 and 106, an ammeter 107 lying between one (106) of the fixed contact pairs and a first output 101 and a second output 102 which is connected to the other fixed contact pair 105 of the pole-changer switch 104. The first output 101 is connected through the lead 72, the appliance connector 71 and the conductive connection 70 with the electrode blocks 65 of the sensors 61, 62, 63, 64 and the second output 102 is connected through a lead 73 with the component 1 to be examined, so that a sensor situated in the operative position, for example the sensor 62 in FIG. 1, of which the small sponge 67 impregnated with an electrolyte, for example an aqueous solution of oxalic acid, rests on the surface region 3 of the component 1 to be examined, forms an electrolytic cell together with the component 1, while the electrolytic current can be read off the ammeter 107 and the cell voltage can be read off a voltmeter 108 connected to the outputs 101 and 102. The electrode blocks 65 of the sensors 61, 62, 63, 64 are here manufactured from a material or a combination of materials which guarantees that during electrolysis under the predetermined working conditions metal ions can never arrive as impurities from the electrode blocks to the component 1 forming the counterelectrode. In most cases the electrode blocks 65 may for example consist of chromium steel.

For sample-taking, which can take place on a conjecturally heavily contaminated reactor component in situ, that is to say in the radiation protection space, the sample-taking appliance is fitted by means of externally operated grippers on to the component so that the bottom opening 27 of the raised housing 25 lies over the surface region to be examined. The small sponges 67 of the sensors 61, 62, 63, 64 are impregnated with electrolyte and the first sensor 61 with the largest sponge application area 68 is situated in the working position, that is to say it lies in the housing opening 27. If the component 1 carries an oxide layer 2 the pole-changer switch 104 is set so that the component 1 is the cathode and the electrode block 65 of the sensor 61 is the anode of the electrolytic cell. In order to provide reproducible conditions, a desired value is predetermined for the cell voltage. By setting of the three-position switch 40 to "down", the housing 25 with the sensor carrier 50 is lowered and when the small sponge 67 of the sensor 61 comes into contact with the component surface the cell actual voltage is observed on the voltmeter 108 and as soon as the cell voltage reaches the predetermined desired value the housing 25 is halted by setting of the three-position switch 49 to "off" and a time switch, for example a stop watch, is set in motion for a time measurement. The electrolytic cell with the small sponge having in the above example an application area of 4 cm² delivers a constant electrolytic current of for example, 0.4 A and an electrochemical reduction of the metal oxide of the oxide layer 2 takes place in accordance with the reactions occurring at the cathode $2H^+ + 2e \rightarrow 2\ H$ and $2\ H + MeO \rightarrow Me\ (metal) + H_2O$ When the oxide layer 4 is dissolved, which is signalled by a sharp rise of the cell voltage on the voltmeter 108, the time switch is stopped and the housing 25 is raised by switching of the three-position switch 49 to "up". Since metal is now present in the surface region 3 to be examined, the pole-changer switch 104 is changed over so that the component 1 becomes the anode. The second sensor 62 is brought into the working position and, as described above, the housing 25 is lowered until the actual value of the cell voltage is equal to the predetermined desired value. The electrolysis is carried out during a time interval t (and the product of electrolytic current I multiplied by time t is ascertained), whereby a metal layer is removed from the component 1 and the removed metal is deposited on the electrode block and absorbed in the small sponge. As is known, Faraday's Law is valid for the theoretical relationship between the magnitude of electric current which has slowed and the reaction products deposited in the sensor, thus $I \cdot t = m/M \cdot n \cdot F$, where m is the weight of the deposited reaction products, M the molecular weight, n the valency variation and F the Faraday constant, but in practice generally deviations occur from it which can be detected in electrolytic efficiency calibration curves without difficulty and with the desired accuracy.

Then two further metal layers are removed from the component with the third and fourth sensors 63 and 64. From the measured values obtained it is possible to ascertain the thickness of the oxide layer and of the three removed metal layers by reference to calibration curves.

After the sample-taking has occurred in this way the housing 25 is expediently closed with a cover, taken out of the frame of the appliance and transferred to suitable measurement appliances for the determination of the activity of the radioactive substances absorbed by the small sponges of the individual sensors 61, 62, 63, 64 and/or for the ascertaining of the chemical composition, often varying with depth, of the metal layers close to the surface.

Figure 2:
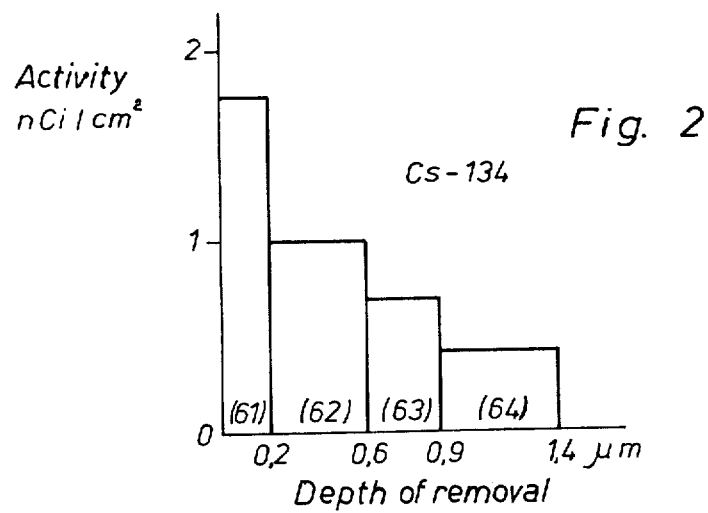
FIG. 2 is an activity profile diagram or graph.

FIG. 2 shows an activity profile thus obtained, where the depth of removal (layer thickness) is entered on the abscissa and the activity is entered on the ordinate in nCi/cm².

FIGS. 3 to 6 show a practical embodiment for a sample-taking appliance according to the invention which is assembled in essence like the appliance shown in FIG. 1.

The frame 5 of the appliance comprises a lower part 5a serving to receive the housing 25 with the sensor carrier 50 formed as turntable (FIG. 1), and an upper part 5b in which the elevating device with the screw jack 41, the drive gear wheels 42, 45 and the electric motor 44 with accessories are accommodated. In the lower frame part 5a two correspondingly short carrier plate-like walls 6 are interconnected at the top by a carrier plate 12 and at the bottom each is provided with a laterally protruding foot 7. The feet 7 are equipped with holding magnets 8. For each holding magnet 8 a magnet lever 10 is pivotably mounted in a bracket 9 on the carrier wall 6, by means of which the magnet 8 is raised and thus the magnetic holding or attraction is released when the magnet lever 9 is pressed in opposition to the biasing force of a return spring 11 against the carrier wall. The upper chassis part 5b is assembled from spacer bolts 14, 16 and spacer sleeves 15 arranged at the four corners of the mounting plate 12, and bearing plates 17, 18 arranged between these, as may be seen from FIG. 3. A hood 19 with a hood lid 20 may be set upon the upper frame part 5b in order to protect the internal components. The carrier plate 12 has a laterally projecting connector bolt 21 (FIG. 4) to which the rod linkage of a conventional remotely-operable device for the operation of the appliance can be attached.

The relatively shallow, parallelepipedic housing 25 with the bottom opening 27 is closable with a housing cover 29 (FIG. 4) which can be mounted from below with a gasket 30 on the housing 25 and held fast by screws guided in lateral protuberances 31, 32 on the housing 25 and on the housing cover 29. The housing 25 with the housing lid 29 forms a closed cassette containing the sensor carrier with the sensors 61, 62, 63, 64, which is filled with electrolyte for the impregnation of the small sensor sponges and from which the electrolyte is removed by removal of the housing cover when the sample-taking appliance is at the examination site.

The drive gear wheel 42 for the screw spindle 41 is eccentrically mounted by means of a bearing plate 43 in the upper bearing plate 18 (FIG. 4). The motor shaft 44a of the electric motor 44 secured above the upper bearing plate 18 in the upper frame part 5b carries output gear wheel 45 which is mounted in the two bearing plates 17 and 18 and meshes with the drive gear wheel 42. A rod 33 is secured at the upper side 26 of the housing 25 and is conducted through a bore 13 in the middle of the carrier plate 12; its upper end is connected by a coupling member 34 with the lower end of the threaded spindle 41 so that the latter cannot rotate about its axis. The rod 33 is detachably secured in the coupling member 34, for example by means of a screw 35 so that (after slackening of the screw 35) the housing 25 can be taken out of the frame of the appliance. The length of the stroke of the threaded spindle 41 is determined by a limit switch 36 which, when the motor is switched to upward movement, is actuated by the correspondingly formed upper end 41a of the threaded spindle 41 and then switches the motor off or over to downward movement. For safety reasons, in order to preclude damage to the appliance, the downward stroke may also be limited by a limit switch.

The shaft 52 of the sensor carrier 50 is rotatably mounted by means of bearing flanges 37a, 37b in the mutually opposite side walls 27a, 27b of the housing 25 and protrudes from the one housing wall 28b (FIG. 3). To enable the housing 25 to be raised and lowered the frame carrier wall 6 associated with this housing wall 28b has a slot 22 (FIG. 6) which is downwardly open in order that the housing 25 may be inserted into and removed from the lower frame part 5a.

A stepping wheel 53 is secured on the project end 52a of the sensor carrier shaft 52 and externally of the carrier wall 6b (FIG. 6) a shift rod 54 is arranged for pivoting about a pivot point 55 and is pressed by a prestressed spring 56 against the stepping wheel 53. At every upward stroke of the housing 25 the stepping wheel 53 is rotated by the shift rod 54 through 90° and thus the next following sensor in each case is brought into its working position.

The approximately square rotary plate 51 of the sensor carrier 50 has a recess 57 at the middle of each side (FIG. 4), into which a sensor is inserted with its shank 66 (FIG. 1). On the one face the rotating plate 51 carries a printed circuit board 58 with contact tracks in contact with the sensor shanks 66, which tracks are not illustrated for the sake of greater clarity, and in the interior of the housing 25 a contact spring 59 is secured (FIG. 3), which connects the sensor that is actually disposed in the working position to the connector 71 (FIG. 1) via the printed circuit board 58.

The preferred embodiment of a sample-taking appliance according to the invention as described above is distinguished by especially simple operation, which is significant especially in the case of sampling in situ and guarantees reliable working, while despite the robustness of the appliance especially the application of the sensor sponges to the surface region to be examined takes place so exactly that the application areas of different sizes lie concentrically on one another and thus in the removal of the individual sample layers contamination of the edge of one layer by active material entrained with the layer thereabove and "crater effects" are avoided in electrolysis and reproducible results are obtained.

The sample-taking appliance may also be used for carrying out so-called wipe tests, in which relatively easily removable material resting on the component surface is taken up by wiping away. The small sponge used for this purpose then preferably has a greater thickness, about double to treble.

It may happen that heavy radioactive particles (a few röntgen) occur which would, for example, falsify the measurements. Such particles or particle conglomerates can likewise be removed without difficulty by the sample-taking appliance. Thus a pac provided with an adhesive coating may for example be fitted on the electrode block of a sensor and the heavy radioactive particles present in the surface region to be examined can be absorbed by means of the adhesive coating and transferred to e.g. a photographic plate for examination.

The external circuitry for such a sample-taking appliance is expediently combined in an easily operable assembly. The drive motor for the spindle will preferably by a low-voltage direct-current motor, so that it can be connected to the direct-current source for the sensors.

I claim:

1. A remotely-operable sample-taking appliance, especially for ascertaining radioactivity profiles in contaminated material surfaces and the chemical composition of strata close to the surface, in which a layer of material is removed electrolytically from the surface region to be examined for each sample by means of a sensor containing a sponge impregnated with an electrolyte, and in that the removed material is absorbed in the sensor sponge for a subsequent chemical analysis and/or analysis of its radioactivity, in order to produce an activity profile of the surface region from a plurality of successive samples, the improvement comprising at least three sensors, a common current connector connected to said sensors, sponges of graduated sizes of application areas associated respectively with said sensors, a sensor carrier carrying said sensors, an appliance framework in which said carrier is arranged for upward and downward movement, and remotely operable setting devices and lifting devices arranged on the framework and effective to bring the individual sensors successively and sequentially in the order of a decreasing sponge application area into a working position and thereafter to lower the sensor in said working position with the sensor carrier to an operative position with defined application pressure of its sponge on the surface region to be examined.

2. An appliance according to claim 1, wherein a housing accommodates the sensor carrier and is movable upwardly and downwardly in the framework, said housing having an underside which is open but closable by a cover to form a closed transport unit for the sensors.

3. An appliance according to claim 2, wherein the housing is liquid-tight when closed with the said cover and is filled with electrolyte for the impregnation of the sensor sponges before the sample taking operation.

4. An appliance according to claim 1, wherein the sensor carrier is a turntable rotatable in the housing about an axis of rotation; a rotary plate is secured to the turntable and carries the sensors in an equally spaced arrangement at its circumference; the said setting device for the setting of the sensors into the working position being arranged for the rotation of the turntable about the said axis.

5. An appliance according to claim 4, wherein the turntable is rotatable in the housing about said axis which is perpendicular to the direction of travel of the housing in the said framework, each sensor being located in its working position when in the course of its rotation the turntable has arrived at the lower point of culmination of the latter.

6. An appliance according to claim 4, wherein the turntable includes a shaft rotatably mounted in the housing, one end of said shaft protruding from the housing, a shift rod pivotably arranged on said framework, and a stepping wheel arranged on the protruding end of said shaft and co-operating with said shift rod to rotate the turntable further by one sensor position during the upward stroke of the housing.

7. An appliance according to claim 1, wherein said framework includes a threaded spindle connectable to be driven by a motor for the upward and downward movement of the sensor carrier.

8. An appliance according to claim 7, wherein said motor is an electric motor and a limit switch is associated in the uppermost position with the threaded spindle by the actuation of which switch the drive motor is switched off or reversed in direction of rotation.

9. An appliance according to claim 1, wherein said framework includes feet in the form of vacuum suction cups or holding magnets for rigidly holding the framework on a base.

10. An appliance according to claim 1 wherein said sensors are four in number and are exchangeably mounted on said sensor carrier.

* * * * *